United States Patent [19]
Petkau et al.

[11] 3,992,513
[45] Nov. 16, 1976

[54] LABELLED PHOSPHOLIPID MATERIAL COLLOIDIALLY DISPERSED AND SIZED TO LOCALIZE AT PRESELECTED ORGANS

[75] Inventors: Abram Petkau, Pinawa; Stanley Daniel Pleskach, Beausejour, both of Canada

[73] Assignee: Atomic Energy of Canada Limited, Ottawa, Canada

[22] Filed: Jan. 7, 1975

[21] Appl. No.: 539,134

[52] U.S. Cl. .................................. 424/1; 128/2 A; 250/303; 252/301.1 R; 252/311; 252/312; 260/403
[51] Int. Cl.² ................. A61K 29/00; A61K 43/00; A61B 10/00; A23J 7/00
[58] Field of Search ........... 424/1; 23/199; 252/252, 252/301.1 R; 260/403; 250/303

[56] References Cited
UNITED STATES PATENTS

| | | | |
|---|---|---|---|
| 3,597,455 | 8/1971 | Arons et al. | 260/403 |
| 3,663,685 | 5/1972 | Evans | 424/1 |
| 3,863,004 | 1/1975 | Wolfangel | 424/1 |
| 3,872,226 | 3/1975 | Haney et al. | 424/1 |

*Primary Examiner*—Benjamin R. Padgett
*Assistant Examiner*—Christine M. Nucker
*Attorney, Agent, or Firm*—Lawrence I. Field

[57] ABSTRACT

A carrier is disclosed for diagnostic scanning agents labelled with short-lived radioisotopes for medical organ studies which comprises colloidally dispersed phospholipid material, and also disclosed are new diagnostic scanning agents utilizing the carrier and a radioisotope, preferably $^{99m}$Tc, which is in a form which complexes with the carrier. The radioisotope labelling can be carried out directly before use, the carrier in dispersed form being stable for a considerable period of time. Methods of preparation of the scanning agents are also disclosed which provide a material which localizes mainly in the liver after injection, or alternately at least initially in the lungs when an aggregating agent is used during preparation in a specific sequence of steps. Specific organ scans or sequential scanning is thus possible.

23 Claims, No Drawings

LABELLED PHOSPHOLIPID MATERIAL COLLOIDIALLY DISPERSED AND SIZED TO LOCALIZE AT PRESELECTED ORGANS

This invention relates generally to medical scanning studies using materials labelled with radioisotopes. More particularly it relates to the use of technetium 99m with particular carrier materials and control of localization of the labelled carrier within the body by specific methods of preparation of the scanning agent.

BACKGROUND OF THE INVENTION

Technetium 99m is widely used in the field of nuclear medicine to visualize internal organs with appropriate scintillation scanning equipment. Its short physical half-life (six hours) and low energy gamma ray (140 kev) make it particularly suitable for such use as the radiation dose to the patient undergoing the diagnostic procedure is minimized. Furthermore, generators are commercially available from which this isotope can be eluted from its parent, 2.7 day molybdenum 99, enabling use of the isotope at great distances from the production site. However, its short physical half-life precludes lengthy or involved preparatory procedures and makes it imperative that they be efficient and brief.

$^{99m}$Tc in the chemical form of pertechnetate ($TcO_4^-$) ion has been used to image some areas of the body, but the biological distribution of the isotope in this form is of an imperfect nature. However, when the technetium is reduced to lower oxidation states it can be efficiently bonded to colloidal material and is then useful for studies of, for example, lung or liver function.

A variety of carries for this isotope have been developed for use in visualizing different organs. For instance $^{99m}$Tc-sulfur colloid preparations are known for use in obtaining liver scans but are not ideal in that they involve a protracted period of mixing, heating, and cooling and the particles are not very uniform as to shape or size. Uniformity of shape and size is important for control of radioisotope content, localization in the body and time of elimination from the body. U.S. Pat. No. 3,683,066 is directed to a kit for use in preparing $^{99m}$Tc-sulfur colloid.

$^{99m}$Tc labelled macroaggregated albumin is widely used for lung scans but might be improved upon as allergenic reactions may occur. U.S. Pat. Nos. 3,663,686 and 3,663,687 are directed to the use of spherical particles of parenterally metabolizable protein as the carrier for radioisotopes such as $^{99m}$Tc. They relate particularly to the preparation of the spherical particles to control the size range, the radioactive labelling process being carried out either before or after particle formation. The control of particle size range is for the purpose of controlling localization within the body. The particle size range is determined, however, during formation of the spherical particles by controlling parameters relating to dispersion of the protein in a suitable liquid. Proteins such as albumin, gelatin, hemoglobin and the like are indicated.

U.S. Pat. Nos. 3,663,687 and 3,725,295 disclose reduction of the $^{99m}$ pertechnetate ion to a lower oxidation state for combination with carrier, using for example ascorbic acid and ferric ion, or stannous ion as the reducing agent.

A recently published article, "Distribution and Fate of Synthetic Lipid Vesicles in the Mouse: A Combined Radionuclide and Spin Label Study," I. R. McDougall et al, Proc. Nat. Acad. Sci. USA 71, No. 9 pp 3487–3491, Sept. 1974, describes the distribution in the mouse of lipid material using $^{99m}$Tc as tracer. The tracer is in the form of pertechnetate anion and is encapsulated within lipid membrane enclosed compartments. These vesicles can be easily disrupted, however, in the body and then the tracer is transported independently of the carrier.

SUMMARY OF THE INVENTION

According to the present invention diagnostic scanning agents for medical purposes are provided which depend on the use of specific carrier material which is metabolizable in the body. The carrier is phospholipid material which is prepared as a colloidal suspension having desired average particle size and narrow size distribution which are easily controlled and standardized. As the carrier material has a natural affinity for multivalent cations, labelling with radioisotope in suitable ionic state for complexing therewith is efficient, and rapid. The labelling of the carrier with radioisotope can be carried out just prior to actual use as a scanning agent, of particular benefit because of the short half-life of radionuclides used for medical scanning purposes. Thus, new diagnostic scanning agents using $^{99m}$Tc and certain other short-lived radioisotopes as for example $^{198}$Au are provided. The invention also provides the carrier material and various reagents required for preparing $^{99m}$Tc-labelled scanning agents in the form of a kit for rapid preparation of the scanning agents just prior to use.

The preferred radioisotope for incorporation into scanning agents according to the invention is $^{99m}$Tc. The preparation of $^{99m}$Tc scanning agents is quickly carried out according to the invention also by virtue of the fact that the reduction of the $^{99m}$Tc as pertechnetate ion, obtained from a commercially available generator, to a lower oxidation stage can be carried out extremely rapidly using a miminum of reagent materials.

Furthermore, the invention provides for the use of an aggregating agent which is added during labelling of the carrier material by a specific sequence of steps. The use of this reagent and its concentration determine the localization of the scanning agent as to whether concentration wll be in the liver or lungs. Thus, carrier material specifically intended for lung scans need not be initially supplied; rather alteration of the localization of the scanning agent as desired can be determined by the steps used when the carrier material is labelled with the radioisotope. By virtue of the concentration of aggregating agent used, it is also possible to utilize the scanning agent for sequential scanning of both lungs and liver.

Thus, the present invention provides an improved approach to the utilization of $^{99m}$Tc and other short-lived radioisotopes as radionuclides in medical tracer applications.

Other advantages of the invention will become apparent from the following description of the preferred embodiment.

DESCRIPTION OF THE PREFERRED EMBODIMENTS

It has been found that phospholipid-containing material in the form of spherical particles of colloidal size (hereinafter referred to as PLS) provides a particularly suitable carrier for radioisotopes, as for example $^{99m}$Tc. The phospholipid material has a natural affinity for bonding of multivalent cations and is metabolizable by the body.

The phospholipid colloidal spheres suitable for use as a radioisotope carrier can be prepared by dispersing suitable phospholipid material in water using conventional procedures involving homogenization, sonication, and centrifugation to provide a supernatant liquid which is a colloidal suspension of the PLS. This colloidal suspension can be used directly for labelling with $^{99m}Tc$ or other radionuclide. The average particle size and size distribution obtained will depend on the time and speed of centrifugation as known in the art. The size distribution can be adjusted as desired by centrifugation or by chromatography to eliminate excessively large or small particles, centrifugation being preferred as it can be carried out under aseptic conditions. Otherwise later sterilization is required. Thus, the PLS are readily prepared having desired particle size and narrow size distribution which can be accurately controlled and standardized for scanning purposes and also for organ function studies.

The average particle size should be such as will be small enough to permit localization in the liver after intravenous injection if that is the organ to be scanned. The localization being to a degree sufficient to provide well-defined scanning using as low a dose of radioisotope as possible with reproducibility of results. It is thus highly desirable to have small particle size and a limited size distribution, i.e. uniformity of particle size. The particle size can of course be made larger on dispersion if localization elsewhere in the body is desired. However, for liver scanning and studies, the carrier material after dispersion suitably has an average particle diameter of 21nm, with a standard deviation of ±5 nm, in the overall range of 13 to 39nm, at which size the PLS localize in the liver when injected intravenously for example into experimental animals such as mice, rats, and dogs.

Suitable concentration of the colloidal suspension of PLS to be labelled with radioisotope is of the order of about 10 to 100 mg per ml, the lower figure being preferred. The concentration will depend to some extent on the particular phospholipid material used but it has been found in animal experiments that the concentration of about 10 to 20 mg per ml provides the most efficient localization of the radioisotope embodied in the scanning agents of the present invention.

Once the PLS have been prepared the colloidal suspension without additives has a shelf life of at least three weeks or more at 4° C without the age of the prepared material having any significant effect on its use in localization of radioisotope in organ studies. During storage however, the particle size tends to increase by aggregation and after about three weeks the localization in the animal liver starts to slowly decrease but even then it does not become very significant for some time, for example as long as three months.

The phospholipids which are suitable as carriers in the instant invention are mixtures of naturally-occurring lecithins, cephalins, plasmogens, glycolipids, and derivatives of phosphatidic acid. The major components are the lecithins as for example phosphatidyl choline, and cephalins as for example phosphatidyl ethanolamine. These substances can of course be prepared by synthetic routes but because of cost, complexity of purification and other reasons the naturally occurring materials from sources such as soybeans, corn oil and other vegetable oils, are by far the most practical for the purposes of the present invention.

Examples of suitable phospholipid material are Asolectin which is a 95% purified preparation of soybean phosphatides supplied by Associated Concentrates, Woodside, Long Island, N.Y. as a dry powder and Intralipid (Trademark), a 10% fat emulsion containing fractionated soybean oil, fractionated egg lecithin, and glycerol, supplied by Pharmacie (Canada) Limited, Montreal, Que. The former material was, however, found to be more suitable for use as carrier material in the scanning agents and is preferred.

For labelling of the carrier with $^{99m}Tc$, this radionuclide is conveniently available in solution in the form of the chemically stable pertechnetate ion ($TcO_4^-$) and can be eluted by saline or dilute acid solution from the parent molybdenum 99 in a generator or "cow." The generators are well known and are commercially available in various forms. For the purposes of the present invention the $^{99m}Tc$ can be eluted with dilute acid, for example HCl, and if necessary the eluate flash evaporated to concentrate it, when for example the activity of the cow is decreased. Thus, a sample of $^{99m}Tc$ of the desired activity can be obtained.

The pertechnetate ion is a monovalent anion which is only loosely bound to the PLS and, in the physiological milieu of animals, is readily dissociated from it. Therefore when administered with PLS, the $^{99m}TcO_4^-$ is distributed generally in the body and little localization of the radioactivity occurs in for example the liver, spleen, or lung although the PLS itself may be localized. However, when $^{99m}Tc$ is reduced to a lower valence state such as IV or V and complexed in cationic form with the PLS, it is bound more firmly and retained by the PLS after injection into the animal system. Thus, it is localized with the carrier in a manner suitable for scanning and diagnostic purposes.

It has been found that the $^{99m}Tc$ as eluted from the $^{99}Mo$ generator in the form of pertechnetate ion can be rapidly reduced to a lower oxidation state with the use of concentrated hydrochloric acid which it is thought reduces the Tc from valence state VII to V. The concentrated HCl is used in large excess and the time of reduction is typically only about 30 seconds to 1 minute but may be longer depending on the quality of the generator. The resulting solution is then buffered and neutralized to pH7. Any method of reduction of the Tc to a lower oxidation state can be used provided of course that the resulting solution is nontoxic on injection Tc can be reduced to the IV oxidation state by addition of, for example, stannous chloride. The preferred method of reduction of the Tc for the purposes of the present invention however is to the V oxidation state by the use of concentrated HCl as it is rapidly effected with a minimum of added material and on neutralization provides a non-toxic solution.

The solution containing $^{99m}Tc$ in the reduced oxidation state can then be utilized directly for complexing of the $^{99m}Tc$ with the colloidal suspension of PLS. Efficient labelling with $^{99m}Tc$ is achieved merely by mixing neutralized $^{99m}Tc$ solution as described, in an amount sufficient to provide the desired scanning activity, with PLS suspension in suitable quantity for injection. The mixing can be done at room temperature and need only be carried out for a few minutes. Thus, it can be carried out directly before actual use of the material as a scanning agent.

It is evident of course that the foregoing procedures for preparation of the scanning agents must be carried out where possible using sterile techniques or at some stage sterilization carried out before actual use of the scanning agent.

When the scanning agent is prepared as described and injected intravenously, it is localized predominately in the liver as measured about 15–30 minutes after injection. Of the order of about 75 to 85% of the total $^{99m}$Tc dose injected is thus localized in animals such as mice, rats and dogs. Furthermore, the reproducibility of localization in these animals is within about 5% at the aforementioned uptake range.

The previous description herein relates to a $^{99m}$Tc scanning agent which is useful for liver function studies. However, by simple modification during preparation of the scanning agent, the localization of the $^{99m}$Tc labelled phospholipid material in the animal can be altered. This can be done by controlled aggregation of the PLS which have been prepared to a size suitable for concentration in the liver, by the addition of specific reagents at a particular stage in the preparation of the scanning agent. The site of localization after injection can be shifted to the lungs rather than the liver as the aggregate size is then such that the largest proportion of the labelled material at least initially does not pass the pulmonary circulation, that is the aggregates are physically stopped in the microcirculation of the pulmonary vasculature. The concentration of the aggregating agent used affects the localization of the scanning agent in the lungs and liver, there being a reciprocal relationship between uptake in these two organs, with no significant change in activity by localization in other parts of the body or losses due to other factors. That is, localization of the scanning agent can be effected initially in the lungs followed by release therefrom and subsequent localization in the liver providing for sequential scanning of these organs, or the localization in the lungs can be effected so that the scanning agent is retained for an extended period of time allowing for repeated lung scans to be carried out. The concentration of aggregating agent used is higher for the latter end purpose than for the former.

Aggregation of the phospholipid spheres may be carried out by addition of divalent cations as for example Ca$^{++}$ and Mg$^{++}$. The complimentary anions of salts of these cations must not be large, toxic, or interfere with the sorption of the cations on the surface of the phospholipid spheres or render the PLS unstable. Suitable compounds for use as aggregating agents are for example calcium chloride and calcium gluconate although the chloride is preferred.

The degree of aggregation, or increase in particle size increases with concentration of the agent. Suitable concentrations of aggregating agents depend somewhat on the specific compound used, the particular phospholipid material and its concentration, and of course the purpose of the use of the scanning agent. For example, with a PLS concentration in the range 10–100 mg per ml the final concentration of the aggregating agent used is millimolar and is suitably of the order of 100 to 400 mM. Size of particles and aggregates begins to increase rapidly with CaCl$_2$ concentration above about 10mM, and at 100–400 mM CaCl$_2$ the average particle size increases from for example an initial value of 21 nm to a range of about 25–125 $\mu$ which at least in experimental animals is sufficiently large for the material to concentrate mainly in the lungs.

The variation in mean diameter of the aggregated particles is more specifically illustrated by the following data. When calcium chloride is added to the $^{99m}$Tc(V) and then the PLS (original mean diameter of 21± 5nm) are introduced, the mean aggregate size at 25 mM CaCl$_2$ is 52.5 microns and increases semilogarithmically to 122 microns at a CaCl$_2$ concentration of 400mM. The equation is of the form $$y = a\, e^{\,bx}$$

where
 $y$ = mean diameter of the $^{99m}$TcPLS aggregates in microns
 $x$ = CaCl$_2$ concentration (mM)
 $a$ = 52.5 microns
 $b$ = 0.00206

When the $^{99m}$Tc(V) is first mixed with the PLS and then the CaCl$_2$ added, the mean aggregate diameter at 25 mM CaCl$_2$ is 85 microns and increases semilogarithmically to 125 microns at 400 mM CaCl$_2$. The equation is of the form $$y = c\, e^{\,dx}$$

where
 $y$ = mean diameter of the $^{99m}$Tc(V)PLS aggregates in microns
 $x$ = CaCl$_2$ concentration (mM)
 $c$ = 85 microns
 $d$ = 0.0012

The localization of the scanning agent in animal lungs as opposed to the liver, is however dependent on the order of addition of the ingredients in the preparation of the agent as well as on the concentration. When the aggregating agent is first mixed with the $^{99m}$Tc, and then the PLS added for labelling which is the preferred sequence localization occurs primarily in the animal lungs on injection. This additional step in the preparation is readily carried out by addition of the aggregating agent in appropriate concentration to the $^{99m}$Tc solution followed by thorough mixing. The PLS can then be labelled with the radioisotope as previously described. However, when the aggregating agent is added after the PLS have been labelled with $^{99m}$Tc, there is not a well-defined effect and the addition may in some cases even enhance localization of the scanning agent in the liver. It appears in this case that time of measurement after injection is critical as the scanning agent initially concentrates in the lungs but the aggregates are rapidly broken down and the material is then transported to the liver. A scanning agent prepared in this manner could be suitable for lung scans and also sequential scanning but such agents are preferably prepared in a different manner, that is by control of time of localization of agent in the lungs by adjustment of concentration of aggregating agent as previously indicated in conjunction with the aforementioned preferred sequence of addition of ingredients.

It has been found that the scanning agents according to the invention have useful stability after preparation. For example, when the PLS are labelled with $^{99m}$Tc to provide a liver scanning agent the stability is at least two hours. Once a $^{99m}$Tc-PLS-CaCl$_2$ aggregated lung scanning agent has been prepared it has been found to be functionally stable for at least 5 ½ hours. Of course, if greater amounts than about 25 mM of aggregating agent are added to the PLS suspension, precipitation occurs immediately but it is only necessary that the material be shaken up to re-suspend the PLS for injection.

The invention is illustrated by the following specific Examples which however are not to be taken as limiting to the scope thereof. The procedures for preparation of the scanning agents were carried out in all cases so as to provide a sterile material suitable for i.v. injection. Conventional procedures and scintillation counting equipment were used to determine radioisotope uptake values.

EXAMPLE 1

A. Preparation of PLS 1 gram Asolectin (95% purified preparation of soybean phosphatides) was dispersed in 30 ml distilled water, homogenized for five minutes in a tissue homogenizer with Teflon pestle, sonicated for one hour in a bath-type sonicator (Aerograph Ultrasonic Cleaner), and then centrifuged in a Ti50 rotor at 42,000 r.p.m. (105,000 × G) for 30 minutes at 5° C. The supernatant containing the PLS had a phospholipid content of 11 mg per ml and contained phospholipid spheres of fairly uniform size with an average diameter of 21 ± 5nm (± value is equal to one standard deviation).

B. Preparation of $^{99m}Tc(V)$ $^{99m}Tc$ radionuclide was obtained in the pertechnetate ($TcO_4^-$) form by elution with 20 ml of 0.1 N HCl from a $^{99}Mo$ "cow" supplied by Commercial Products, Atomic Energy of Canada Limited, Ottowa, Canada. 0.1 ml of the eluate was acidified with 1 ml of 12N HCl and allowed to stand for a period of time, which in a series of experiments was varied from 10 seconds to 25 minutes. This was followed by partial neutralization with 1 ml of 12N NaOH, buffering with 1 ml of 0.5M $KH_2PO_4$, and finally neutralization to pH7 with 3M NaOH. The resulting solution contained $^{99m}Tc$ reduced to the V valence state (reference: Eckelmen et al., *J. Nuclear Med.* 13 No. 8 (1972) p 577–581).

C. Labeling of PLS with $^{99m}Tc$

An amount of 0.1 ml of the $^{99m}Tc(V)$ obtained in part B. having an activity of approximately 0.1 microcurie was added to 1 ml of the colloidal suspension of PLS obtained in part A and thoroughly mixed. Labelling with the radioisotope was at least 98% complete as shown by data from experiments where the $^{99m}Tc$-PLS complex was precipitated with 25mM $CaCl_2$ and the residual amount of unbound $^{99m}Tc$ in the supernatant determined.

D. A series of experiments were carried out wherein 0.05 ml (approximately $10^5$ cpm in activity) of each sample of $^{99m}Tc$ labelled PLS from Part C was used for intravenous injection using mice as the experimental animals. The biological distribution of the $^{99m}Tc$ was determined 30 minutes after intravenous injection in each case. The results are shown in Table I.

TABLE I

Effect of variable reduction time on liver uptake of $^{99m}Tc(V)PLS$ in the mouse.

| $Tc(VII) \rightarrow Tc(V)$ Reduction time | Volume Injected (ml) | % Uptake of total body dose of $^{99m}Tc(V)PLS$ Liver |
|---|---|---|
| 10 sec | 0.05 | 74 ± 2.7 |
| 30 sec | 0.05 | 73.5 ± 1.5 |
| 1 min | 0.05 | 74 ± 2.2 |
| 2 min | 0.05 | 58 ± 2.0 |
| 5 min | 0.05 | 63 |
| 10 min | 0.05 | 55 |
| 15 min | 0.05 | 61 |
| 20 min | 0.05 | 56 |
| 25 min | 0.05 | 53 |

From the Table it can be seen that the $^{99m}Tc$ (V) PLS prepared as described concentrates mainly in the liver and provides an effective scanning agent for that organ. The Table also shows the effect of the time of reduction of the Tc to valence state V on the liver uptake, and that a period of only 30 seconds to 1 minute is sufficient for carrying out the reduction process. It was also found that the liver uptake was independent of volume of sample injected.

EXAMPLE 2

Stability of PLS suspension.

A PLS suspension was prepared as described in Example 1A and stored in a refrigerator at 4° C. At various time intervals thereafter aliquots were taken, labelled with $^{99m}Tc$ as described in Examples 1B and 1C and tested for liver uptake in mice as experimental animals. The results are shown in Table II.

TABLE II

Mean Particle Diameter of Phospholipid Spheres and their capacity to Localize $^{99m}Tc$ in the Mouse Liver as a Function of Storage at 4° C.

| Storage time (days) | Mean Particle Diameter μ | Capacity to Localize $^{99m}Tc$ in the Liver (% of total amount injected intravenously) |
|---|---|---|
| 1 | 0.025 | 83 |
| 13 | 0.036 | 82.8 |
| 21 | 0.10 | — |
| 27 | 0.11 | 79.3 |
| 34 | 0.13 | — |
| 41 | 0.26 | — |
| 88 | 0.37 | 69 |

From the table it can be seen that enlargement of the PLS occurred very gradually on storage but for a period of at least three weeks there was no significant effect on the radioisotope localization in the mouse liver. Even after three months the change was not great. During storage the PLS remained bacteria-free and exhibited no detectable chemical change, no stabilizer having been added.

EXAMPLE 3

The role of the PLS in the use of the scanning agents according to the invention was shown by comparative experiments. In the first, a scanning agent was prepared according to the procedure of Example 1 and in the second, a $^{99m}$Tc (V) solution as prepared in Example 1 Part B was used by itself. Evaluation was carried out using mice as the experimental animals and the results are shown in Table III.

TABLE III

Dependence of Liver Uptake of $^{99m}$Tc(V) on PLS and the Reduction Process. Volume of sample injected into the mouse was 0.1 ml.

| $^{99m}$Tc(V) Sample preparation | % Uptake of total body dose of $^{99m}$TC Liver |
|---|---|
| $^{99m}$TcO$_4^-$ → $^{99m}$Tc(V) with PLS | 74.2 ± 0.7 |
| $^{99m}$TcO$_4^-$ → $^{99m}$Tc(V) without PLS | 23.5 ± 7 |

The reproducibility of the localization of the scanning agent in the liver was tested by preparing four separate samples each by the procedure of Example 1. Evaluation again was made using mice as the experimental animals and the results are shown in Table IV.

TABLE IV

Reproducibility of the liver uptake of $^{99m}$Tc(V) PLS in the mouse. Samples prepared separately.

| Sample | % Uptake of total body dose of $^{99m}$Tc(V) PLS Liver |
|---|---|
| 1 | 79.0 |
| 2 | 73.0 |
| 3 | 80.6 |
| 4 | 74.0 |

EXAMPLE 4

The biological distribution of $^{99m}$Tc (V) PLS to which an aggregrating agent had been added was tested using mice and rats (~10$^5$ cpm activity injected) as the experimental animals. Calcium chloride was used as the aggregating agent. The preparation in each case was carried out as in Example 1 except for the addition of calcium chloride solution in amounts such that the final concentration in the material for injection was 100 millimolar, the calcium chloride solution being added either to the $^{99m}$Tc solution followed by mixing with the PLS or added after labelling of the PLS with the $^{99m}$Tc. The results are shown in Tables V and VI.

TABLE V

Effect of Addition of CaCl$_2$ to $^{99m}$Tc(V) PLS on Organ Uptake of the Complex in the Mouse. Post-Injection time = 15 min.

| Sample Preparation | % Uptake of total body dose of $^{99m}$TC(V) PLS | |
|---|---|---|
| | Liver ± σ | Lung ± σ |
| $^{99m}$Tc(V) plus PLS | 73 ± 3 | 1.0 ± 0.2 |
| $^{99m}$Tc(V) plus PLS, then added 100 mM CaCl$_2$ | 85 ± 5 | 0.9 ± 0.4 |
| $^{99m}$Tc(V) plus 100 mM CaCl$_2$, then added PLS | 6.9 ± 4.4 | 76 ± 6 |

TABLE VI

Effects of the Addition of CaCl$_2$ to $^{99m}$Tc(V)PLS and of the Post-Injection time on the Relative Uptake by Rat Liver and Lung of $^{99m}$Tc(V)PLS.

| Sample Preparation | Post-Injection time (min) | % Uptake of total body dose of $^{99m}$Tc(V) PLS | |
|---|---|---|---|
| | | Lung | Liver |
| $^{99m}$Tc(V) plus 100 mM CaCl$_2$, then PLS | 10 | 95.1 | 2.4 |
| " | 120 | 88.7 | 8.1 |
| $^{99m}$Tc(V) plus PLS, then 100 mM CaCl$_2$ | 10 | 53.5 | 37.6 |
| " | 120 | 40.2 | 52 |

These Tables clearly show the reciprocal relationship between liver and lung uptake with the use of an aggregating agent added in specific sequence during preparation of the scanning material. The results were confirmed on dogs injected with about 100 to 150 microcuries via an antecubital vein.

EXAMPLE 5

The procedure of Example 4 was used to prepare lung scanning agents, calcium gluconate being used however as the aggregating agent added to the $^{99m}$Tc, followed by mixing with the PLS and complexing. The concentration of calcium gluconate was varied in a series of experiments and a comparative experiment was carried out wherein the PLS was omitted. Evaluation of the scanning agents so prepared was made using mice as experimental animals. The results are shown in Table VII.

TABLE VII

Effect of Calcium Gluconate on the Relative Uptake of $^{99m}$Tc(V)PLS by the Mouse Lung and Liver. Post-injection time = 10 min.

| Sample Preparation | % Uptake of total body dose of $^{99m}$Tc(V) PLS | | |
|---|---|---|---|
| | Lung | Liver | Body |
| $^{99m}$Tc(V) plus 25 mM Ca gluconate, then PLS | 20.6 | 30.9 | 26.6 |
| $^{99m}$Tc(V) plus 50 mM Ca gluconate, then PLS | 56.6 | 26.2 | 18.8 |
| $^{99m}$Tc(V) plus 75 mM Ca gluconate, then PLS | 74.2 | 18.3 | 5.1 |
| $^{99m}$Tc(V) plus 100 mM Ca gluconate, then PLS | 88.0 | 5.1 | 4.0 |
| $^{99m}$Tc(V) plus 100 mM Ca gluconate, no PLS | 61 | 32.2 | 6.7 |

The effect of concentration of aggregating agent on localization of the scanning agent after injection is shown and also the effect of the PLS carrier. Similar results regarding the effect of concentration of aggregating agent on percent uptake were obtained with calcium chloride.

EXAMPLE 6

Experiments were carried out relevant to the retention of the lung scanning agent, according to the invention, with time after injection. Calcium chloride was used as the aggregating agent and the variation in biological distribution in the mouse after injection when the concentration of calcium chloride was 100mM is shown in Table VIII.

TABLE VIII

Effect of Post-Injection Time on the Relative Uptake by Mouse Liver and Lungs of $^{99m}$TcPLS. Scanning agent preparation: $^{99m}$Tc(V) plus 100 mM CaCl$_2$, then PLS.

| Post-Injection time (min) | % Uptake of total body dose of $^{99m}$Tc(V) PLS | | |
|---|---|---|---|
| | Lung | Liver | Body |
| 5 | 81.4 | 3.5 | 13.8 |
| 15 | 96.2 | 2.6 | 0.6 |
| 30 | 96.7 | 2.0 | 0.7 |
| 60 | 95.2 | 3.2 | 0.7 |
| 120 | 89.0 | 5.8 | 1.4 |
| 240 | 94.5 | 3.7 | 0.5 |

The foregoing indicate that the concentration of aggregating agent used determine the retention of the scanning agent in the lungs where it is initially concentrated. By adjusting the concentration of the aggregating agent, the scanning agent can be used for sequential scanning of lungs and liver or for repeated lung scans.

EXAMPLE 7

A series of lung scanning agents were prepared as described in Example 4, the carrier however being prepared from a 10% fat emulsion, sold under the name Intralipid$^R$, which contains 10g% fractionated soybean oil, 1.2 g% fractionated egg lecithin, and 2.5g% glycerol. The carrier was prepared as described in part A of Example 1; however, the dispersion was used without

| Ionization state of $^{99m}$Tc | Post Injection time (min) | % Uptake of total body dose of $^{99m}$TcPLS | | | |
|---|---|---|---|---|---|
| | | Liver | Lung | Liver & Lung | body |
| V | 5 | 11.3 | 79 | 90.3 | 7.4 |
| V | 15 | 34.1 | 55.6 | 89.7 | 4.2 |
| V | 30 | 53.2 | 38 | 91.2 | 4.9 |
| V | 60 | 62.0 | 22.6 | 84.6 | 5.1 |
| V | 120 | 79.8 | 7.3 | 87.1 | 6.1 |

The biological distribution when the concentration of calcium chloride used was 150mM on clearance of the lung scanning agent is shown in Table IX.

TABLE IX

Effect of 150mM CaCl$_2$ on Clearance of $^{99m}$Tc(V)PLS from the Rat Lung. Scanning agent preparation: $^{99m}$Tc(V) plus 150mM CaCl$_2$, then PLS.

centrifugation and the final concentration of the PLS was 97mg per ml. Calcium gluconate and calcium chloride were used as the aggregating agents in different concentrations. Evaluation of the scanning agents so prepared was carried out using mice and the results are shown in Table X.

TABLE X

Effect of Calcium Gluconate and CaCl$_2$ on Organ Localization in mice of $^{99m}$Tc(V) complexed with Uncentrifuged PLS (97 mg/ml) prepared from Intralipid$^R$.

| Sample Preparation | Post-Injection time (min) | % Uptake of total body dose of $^{99m}$Tc(V) PLS | |
|---|---|---|---|
| | | Lung | Liver |
| $^{99m}$Tc(V) plus 150 mM Ca gluconate, then Intralipid PLS | 5 | 68 | 21 |
| $^{99m}$Tc(V) plus 150 mM Ca gluconate, then Intralipid PLS | 15 | 74 | 19 |
| $^{99m}$Tc(V) plus 150 mM Ca gluconate, then Intralipid PLS | 30 | 69 | 25 |
| $^{99m}$Tc(V) plus 150 mM Ca gluconate, then Intralipid PLS | 60 | 67 | 25 |
| $^{99m}$Tc(V) plus 150 mM Ca gluconate, then Intralipid PLS | 90 | 59 | 35 |
| $^{99m}$Tc(V) plus 150 mM Ca gluconate, | | | |

-continued

| Sample Preparation | Post-Injection time (min) | % Uptake of total body dose of $^{99m}$Tc(V) PLS | |
|---|---|---|---|
| | | Lung | Liver |
| then Intralipid PLS | 120 | 67 | 26 |
| $^{99m}$Tc(V) plus 150 mM Ca gluconate, then Intralipid PLS | 180 | 47 | 40 |
| $^{99m}$Tc(V) plus 100 mM CaCl$_2$, then Intralipid PLS | 15 | 64 | 22 |
| $^{99m}$Tc(V) plus 150 mM CaCl$_2$, then Intralipid PLS | 15 | 82 | 6 |
| $^{99m}$Tc(V) plus 175 mM CaCl$_2$, then Intralipid PLS | 15 | 94 | 3 |
| $^{99m}$Tc(V) plus 200 mM CaCl$_2$, then Intralipid PLS | 15 | 96 | 1 |

The use of "Intralipid" as the carrier for the scanning agent is not as effective in localizing the $^{99m}$Tc activity in the lung as the Asolectin despite the much higher concentration. Thus the latter material is preferred as the carrier. The effect on the organ localization by variation in the concentration of calcium chloride is also shown in this Table.

EXAMPLE 8

Triplicate lung scanning agents according to the invention were prepared to determine the effective half-life and biological half-life of the scanning agent in the dog as experimental animal. The results are shown in Table XI.

TABLE XI

Kinetic Analysis of the Clearance of $^{99m}$Tc(V) PLS Activity from the Dog Lung. Volume of sample injected = 5.0 ml.

| Sample Preparation[1] | Body Weight (kg) | $T_{eff}$[2] (h) | $T_b$[3] (h) | Calculated % Uptake of $^{99m}$Tc-(V) PLS in lung[4] |
|---|---|---|---|---|
| $^{99m}$Tc(V) + 400 mM CaCl$_2$, then PLS added | 11.2 | 2.6 | 4.6 | 82 |
| $^{99m}$Tc(V) + 400 mM CaCl$_2$, then PLS added | 10.5 | 4.3 | 14.9 | 75 |
| $^{99m}$Tc(V) + 400 mM CaCl$_2$, then PLS added | 16 | 2.6 | 4.8 | 78 |

[1]$^{99m}$Tc(V) prepared from $^{99m}$TcO$_4^-$ obtained from the Nuclear Medicine Department, Winnipeg General Hospital.
[2]$T_{eff}$ = the effective halflife of $^{99m}$Tc(V) in the dog lung.
[3]$T_b$ = the biological halflife of $^{99m}$Tc(V) in the dog lung.
[4]For a post-injection time of 20 min. The percentage is that of the totalbody dose.

The Table shows that the uptake by the lungs is satisfactory and also that the effective half-life is suitable for scanning purposes. Radioscans of the lung distribution showed that the $^{99m}$Tc is generally distributed throughout both lung fields with little radioactivity localized elsewhere to obscure the visualization of the lungs.

The invention also includes kits for ready preparation of the scanning agents herein described. The kit includes the PLS carrier in aqueous suspension, reducing agent for obtaining $^{99m}$Tc in required cationic lower valence state, and buffering reagent. It may also include any or all of a reagent for eluting $^{99m}$TcO$_4^-$ from a commercial $^{99}$Mo generator, neutralizing reagent, and the aggregating agent as an aqueous solution. From the disclosures herein, it is evident that the preferred eluting reagent is dilute HCl, the preferred reducing agent concentrated HCl, and the preferred aggregating agent calcium chloride as an aqueous solution of concentration suitable for dilution to the desired value. Substitutions in reagents may readily be made on the basis of the disclosure herein and the knowledge of one skilled in the art.

It is understood of course from the foregoing that the preparation of the scanning agents according to the invention is carried out using conventional techniques for the provision of sterile material suitable for intravenous injection.

The embodiments of the invention in which an exclusive property or privelege is claimed are defined as follows:

1. A composition for radioactive isotope localization purposes in medical studies which comprises a carrier consisting of phospholipid material colloidally dispersed in an aqueous medium and having a predetermined particle size so as to localize at preselected organs after injection, said carrier being labelled with a short-lived radioisotope in multivalent cationic form.

2. The composition as claimed in claim 1 wherein the radioisotope is $^{99m}$Tc in a reduced valence state.

3. The composition of claim 1 wherein the average particle size of phospholipid material is sufficient to provide localization predominately in the liver on injection.

4. The composition of claim 3 wherein the average particle size is about 21 ± 5 nm.

5. The composition of claim 4 wherein the concentration of phospholipid material is 10 to 100 mg/ml.

6. The composition as claimed in claim 1 wherein the phospholipid material contains lecithins and cephalins as major components.

7. The composition as claimed in claim 1 wherein the radioisotope is $^{198}$Au.

8. A composition for radioactive isotope localization purposes in medical studies which comprises an aqueous medium containing a carrier consisting of phospholipid material labelled with a short-lived radioisotope in multivalent cationic form and aggregated from initial colloidal dispersion by a metal cation aggregating agent in concentration sufficient to provide an average carrier particle size which will localize predominantly in the lungs on injection.

9. A composition is claimed in claim 8 wherein the metal cation aggregating agent is mixed with the radioisotope before labelling of the carrier therewith.

10. The composition as claimed in claim 9 wherein the aggregating agent is present in millimolar concentration based on total volume.

11. The composition as claimed in claim 10 wherein the concentration of aggregating agent is about 100–400 mM.

12. The composition as claimed in claim 11 wherein the average particle size of phospholipid material is about 25–125 $\mu$.

13. The composition as claimed in claim 9 wherein the aggregating agent is a salt of a divalent cation of the group of Ca and Mg.

14. The composition as claimed in claim 13 wherein the aggregating agent is calcium chloride.

15. The composition as claimed in claim 13 wherein the aggregating agent is calcium gluconate.

16. A process for the preparation of a radioisotopically labelled organ scanning agent comprising complexing a short-lived radioisotope in multivalent cationic form with colloidally dispersed phospholipid material.

17. A process is claimed in claim 16 wherein the radioisotope is $^{99m}Tc$ which as pertechnetate ion is reduced to a lower valence state before complexing with the phospholipid material.

18. A process is claimed in claim 17 wherein the reduction of $^{99m}Tc$ to a lower oxidation state is carried out with concentrated HCl for a period of about 30 seconds to one minute, followed by buffering and neutralization.

19. A process for the preparation of a radioactively labelled lung scanning agent comprising reduction of $^{99m}Tc$ as pertechnetate ion to a lower oxidation state, mixing an aqueous solution of a metal cation aggregating agent therewith, followed by addition of an aqueous colloidal dispersion of phospholipid material and mixing.

20. The process as claimed in claim 19 wherein the average particle size of the dispersed phospholipid material is originally about $21 \pm 5$ nm.

21. The process as claimed in claim 20 wherein the scanning agent contains the dispersed phospholipid material in a concentration of about 10 to 100 mg. per ml.

22. The process as claimed in claim 19 wherein the aggregating agent is a member of the group of calcium chloride and calcium gluconate.

23. The process is claimed in claim 22 wherein the aggregating agent is present in the scanning agent in a concentration of about 100 to 400 mM.

* * * * *